(12) United States Patent
Fan

(10) Patent No.: US 8,860,979 B2
(45) Date of Patent: Oct. 14, 2014

(54) DELETION OF UNWANTED REPLY MESSAGES IN E-MAIL PRINTING

(75) Inventor: Zhigang Fan, Webster, NY (US)

(73) Assignee: Xerox Corporation, Norwalk, CT (US)

( * ) Notice: Subject to any disclaimer, the term of this patent is extended or adjusted under 35 U.S.C. 154(b) by 1393 days.

(21) Appl. No.: 12/559,732

(22) Filed: Sep. 15, 2009

(65) Prior Publication Data

US 2010/0208290 A1 Aug. 19, 2010

(51) Int. Cl.
*G06F 3/12* (2006.01)
*H04K 1/00* (2006.01)
*G01N 33/68* (2006.01)
*A61K 38/17* (2006.01)
*A61K 49/00* (2006.01)
*C07K 16/40* (2006.01)
*C07K 14/575* (2006.01)

(52) U.S. Cl.
CPC ........ *A61K 38/1709* (2013.01); *G01N 33/6893* (2013.01); *G01N 2800/323* (2013.01); *A61K 49/0004* (2013.01); *C07K 16/40* (2013.01); *C07K 14/575* (2013.01)
USPC .......................................... 358/1.15; 380/255

(58) Field of Classification Search
CPC . A61K 38/1708; A61K 49/0004; C07K 16/40
USPC .......................................... 358/1.15; 380/255
See application file for complete search history.

(56) References Cited

U.S. PATENT DOCUMENTS

| 6,032,004 | A | 2/2000 | Mirabella, Jr. et al. |
| 6,268,926 | B1 | 7/2001 | Okimoto et al. |
| 6,982,801 | B1 | 1/2006 | Saito |
| 7,570,387 | B2 | 8/2009 | Yamaguchi |
| 2004/0201615 | A1 | 10/2004 | Dietz et al. |
| 2006/0044606 | A1* | 3/2006 | Yamamura .................. 358/1.15 |
| 2008/0183823 | A1* | 7/2008 | Valencia ....................... 709/206 |
| 2009/0214034 | A1* | 8/2009 | Mehrotra et al. ............ 380/255 |

* cited by examiner

*Primary Examiner* — Douglas Tran
*Assistant Examiner* — Justin Katzwhite
(74) *Attorney, Agent, or Firm* — Gibb & Riley, LLC

(57) ABSTRACT

Methods and systems receive an instruction to print an accumulation e-mail message through a graphic user interface of a computerized device. The accumulation e-mail comprises an original e-mail message and one or more reply e-mail messages made to the original e-mail message. The methods and systems automatically identify boundaries between the e-mail messages within the accumulation e-mail using the computerized device; automatically truncate the original e-mail message and one or more of the reply e-mail messages from the accumulation e-mail message to create a modified accumulation e-mail message using the computerized device; and automatically print the modified accumulation e-mail message using a printing device.

16 Claims, 4 Drawing Sheets

On Dec 12, 2008, at 10:07 AM, xxx<xxxx@xxx.xxx> wrote:

Header 1

} 301

Xxxx wrote:

Header 2

} 302

From: xxx[mailto:xxxx @xxx.xx]
Sent: Friday, December 12, 2008 11:02 AM
To: xxxx
Cc: xxx <xxx@xxx.xx>
Subject:
Header 3

} 303

>>> <xxx@xxxx.xx> 11/10/2007 10:40 PM >>>

Header 4

} 304

"xxx"<xxx@xxxx.xx>
11-26-2007 13:10        To: xxxxxxx
                        Cc: xxxxxx, xxxx
                            Subject:

Header 5

} 305

Quoting "xxx"<xxx@xxxx.xx>:

Header 6

} 306 xxx@xxxx.xx wrote:

Header 7

} 307

At 17:39 19/6/2006, you wrote:

Header 8

} 308

---------------2006-02-21 09:47:00 ---------------
Header 9

```
                Xxxx <xxx@xxxx.xx>
                   To  xxxxxxxxx
                   Cc xxxxxxxxx                    ⎫
03/05/2008 12:37 pm         Subject    xxxxxxxxxxxx ⎬ 310
                    Header 10                       ⎭

Subject: xxxxxx
                Date: 12/30/2006                    ⎫
                From: xxxxxx                        ⎬ 311
                To: xxxxxx                          ⎭
                    Header 11

--xxx@xxxx.xx --                     ⎫
                ►Jan. 11, 2008                      ⎬ 312
                    Header 12                       ⎭

Xxxx <xxx@xxxx.xx> wrote:               ⎫
                    Header 13                       ⎬ 313

On 1/10/08 xxxx wrote:               ⎫
                    Header 14                       ⎬ 314

============== 2007-12-21 23:15:45 You Write: ================  ⎫ 315
                    Header 15                                    ⎬

============== You Write: =================         ⎫ 316
                    Header 16                       ⎬

----------------Original Message ---------------------  ⎫
            From: xxxx [Mailto xxx@xxxx.xx]                       ⎬ 317
                    Header 17                                     ⎭

On Mon, 30 OCT  2005 16:25:21-0400        ⎫
            "xxxx "<xxx@xxxx.xx> wrote:             ⎬ 318
                    Header 18                       ⎭
```

FIG. 3B

DELETION OF UNWANTED REPLY MESSAGES IN E-MAIL PRINTING

BACKGROUND AND SUMMARY

Embodiments herein generally relate to printing devices such as xerographic or electrostatic printing devices and more particularly relate to methods and systems that reduce the amount of printing resources utilized when printing e-mail messages.

Reducing paper and toner consumption not only saves printing cost, but also benefits the environment. Quite often, a document is printed with information that is not intended to be printed. One such example is e-mail printing. In most e-mail systems, the original incoming message is attached at the bottom when a reply message is composed. If another reply is made to the reply e-mail, it is also added to the string of e-mails as each e-mail is replied to. The string of replies to the original e-mail and the replies to the reply e-mails can be quite extensive. Other systems organize strings of e-mail messages into structures called "conversations". All such files that contain a current e-mail and the preceding e-mail replies from an original e-mail (strings of reply e-mails) are considered "accumulated" e-mail messages in the description herein.

For a message that has experienced multiple RE (reply) iterations, the e-mail file could be very long. Quite often, a user may only be interested in printing out the most recent message or messages, but when the user clicks the print button, the entire history of the interaction containing many pages is printed.

In view of these issues, the embodiments herein provide a method that receives an instruction to print an accumulation e-mail message through a graphic user interface of a computerized device. The "accumulation" e-mail comprises an original e-mail message and one or more reply e-mail messages made to the original e-mail message. The reply e-mail messages can be made to the original e-mail message or to other reply e-mail messages. Thus, the original e-mail message and the reply e-mail messages comprise a historical chronology of replies made to the original e-mail message and to the reply-messages.

The embodiments herein automatically identify boundaries between the e-mail messages within the accumulation e-mail message using the computerized device. For example, the embodiments herein can identify the boundaries by matching pre-established header templates to text within the accumulation e-mail message to identify a beginning point of each e-mail message. The text immediately before the beginning of each e-mail message represents the end of an immediately adjacent e-mail message.

Once in the beginning and ending locations of each e-mail message has been identified, the embodiments herein can automatically truncate (remove, delete) the original e-mail message and one or more of the reply e-mail messages from the accumulation e-mail message to create a modified accumulation e-mail message using the computerized device.

The truncating is based on pre-established truncation rules that can be set up by receiving user truncation preferences. The pre-established truncation rules can be very flexible and provide many different user options. This truncating process can, for example, remove all e-mail messages except the most recent e-mail message from the accumulation e-mail message to create the modified accumulation e-mail message. Alternatively, a certain number of the most recent e-mail messages (2, 4, 6) or a certain number of pages of complete e-mail messages can be allowed to remain within the modified accumulation e-mail message, again depending upon the user truncation preferences. Similarly, the user can set the pre-established truncation rules to only include the original e-mail message and the most recent e-mail message (or a certain number of most recent e-mail messages). One ordinarily skilled in the art would understand from these examples that the user preferences can be very flexible and can include many other choices regarding which e-mail messages are truncated and which e-mail messages are allowed to remain within the modified accumulation e-mail message.

Since the user has provided the instruction to print the accumulation e-mail message, the embodiments herein automatically print the modified accumulation e-mail message using a printing device.

System and device embodiments herein include a processor and a computer-readable storage medium operatively connected to (directly or indirectly connected to) the processor. The computer readable-storage medium stores instructions executable by the processor. A graphic user interface is operatively connected to the processor. The graphic user interface receives the instruction from the user to print the accumulation e-mail message. In addition, a printing device is operatively connected to the processor.

The processor executes the instructions to automatically identify boundaries between the e-mail messages within the accumulation e-mail message by matching pre-established header templates to text within the accumulation e-mail message, so as to identify the beginning point of each e-mail message and the ending point of each subsequent e-mail message.

The processor also executes the instructions to automatically truncate the original e-mail message and one or more of the reply e-mail messages from the accumulation e-mail message to create the modified accumulation e-mail message. In doing so, the processor is following the pre-established truncation rules set up by the user, which can be maintained within the computer-readable storage medium. The processor further executes the instructions to automatically print the modified accumulation e-mail message using the printing device.

These and other features are described in, or are apparent from, the following detailed description.

BRIEF DESCRIPTION OF THE DRAWINGS

Various exemplary embodiments of the systems and methods are described in detail below, with reference to the attached drawing figures, in which:

FIGS. 3A-3B are examples of header templates utilized by embodiments herein.

DETAILED DESCRIPTION

As mentioned above, accumulated e-mail files that contain multiple reply e-mails can be very long. Quite often, a user may only be interested in printing out the most recent message or messages, but when the user clicks the print button, the entire history of the interaction containing many pages is printed unless the user takes many steps to determine on which pages the most recent e-mail(s) is (are) located and to limit the printing to those specific pages.

Figure 1:
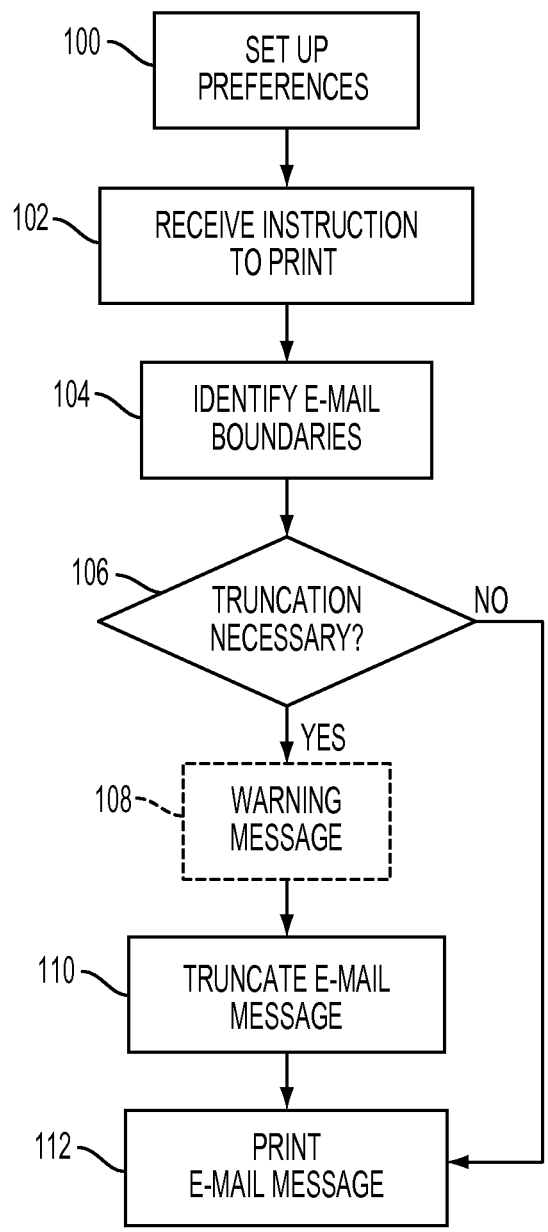
FIG. 1 is a flowchart illustrating methods according to embodiments herein.

In view of these issues, as shown in flowchart form in FIG. 1, the embodiments herein provide a method that solicits or receives user (or default) preferences regarding how the automated process of printing e-mails should be conducted, in item 100. For example, when the embodiments herein are initially utilized by the user (or set up for default settings by the manufacturer) the preferences can be set in item 100 to only print the most recent e-mail, only print the most recent 3 e-mails, only print the most recent e-mail and the original e-mail, to only print the first 5 pages of complete e-mails, etc., or any combination of such limitations.

The method also receives an instruction to print an accumulation e-mail message through a graphic user interface of a computerized device in item 102. The "accumulation" e-mail comprises an original e-mail message and one or more reply e-mail messages made to the original e-mail message. The reply e-mail messages can be made to the original e-mail message or to such reply e-mail messages. Thus, the original e-mail message and the reply e-mail messages comprise a historical chronology of replies made to the original e-mail message and to such reply-messages.

In item 104, the embodiments herein automatically identify boundaries between the e-mail messages within the accumulation e-mail message using the computerized device. For example, the embodiments herein can identify the boundaries by matching pre-established header templates to text within the accumulation e-mail message to identify a beginning point of each e-mail message. The text immediately before the beginning of each e-mail message represents the end of the immediately adjacent (preceding or succeeding) e-mail message.

Once the beginning and ending locations of each e-mail message have been identified, the user preferences are evaluated to determine whether any e-mail messages should be removed in item 106. For example, if the user preferences only allow the last two e-mails to be printed and three e-mails are present in the accumulation e-mail, one of the e-mail messages will have to be truncated from the accumulation e-mail. In that case, processing proceeds to item 108. If truncation is not necessary, the untruncated e-mail is printed in item 112.

A warning message can optionally be provided (as indicated by the dashed box 108 in FIG. 1) to the user giving the user an option of whether to allow the truncation process to proceed. If the user does not stop the automated process in item 108, in item 110 the embodiments herein automatically truncate (remove, delete, crop) the original e-mail message and one or more of the reply e-mail messages from the accumulation e-mail message (according to the preferences set up in item 100) to create a modified accumulation e-mail message using the computerized device.

The truncating 110 is based on the pre-established truncation rules set up in item 100. The pre-established truncation rules can be very flexible and provide many different user options. This truncating process can, for example, remove all e-mail messages except the most recent e-mail message from the accumulation e-mail message to create the modified accumulation e-mail message. Alternatively, a certain number of the most recent e-mail messages (2, 4, 7, etc.) or a certain number of pages of complete e-mail messages can be allowed to remain within the modified accumulation e-mail message, again depending upon the user truncation preferences. Similarly, the user can set the pre-established truncation rules to only include the original e-mail message and the most recent e-mail message (or a certain number of most recent e-mail messages). One ordinarily skilled in the art would understand from these examples that the user preferences can be very flexible and can include many other choices regarding which e-mail messages are truncated and which e-mail messages are allowed to remain within the modified accumulation e-mail message.

Since the user has provided the instruction to print the accumulation e-mail message, the embodiments herein automatically print the unmodified or modified accumulation e-mail message using a printing device in item 112.

Figure 2:
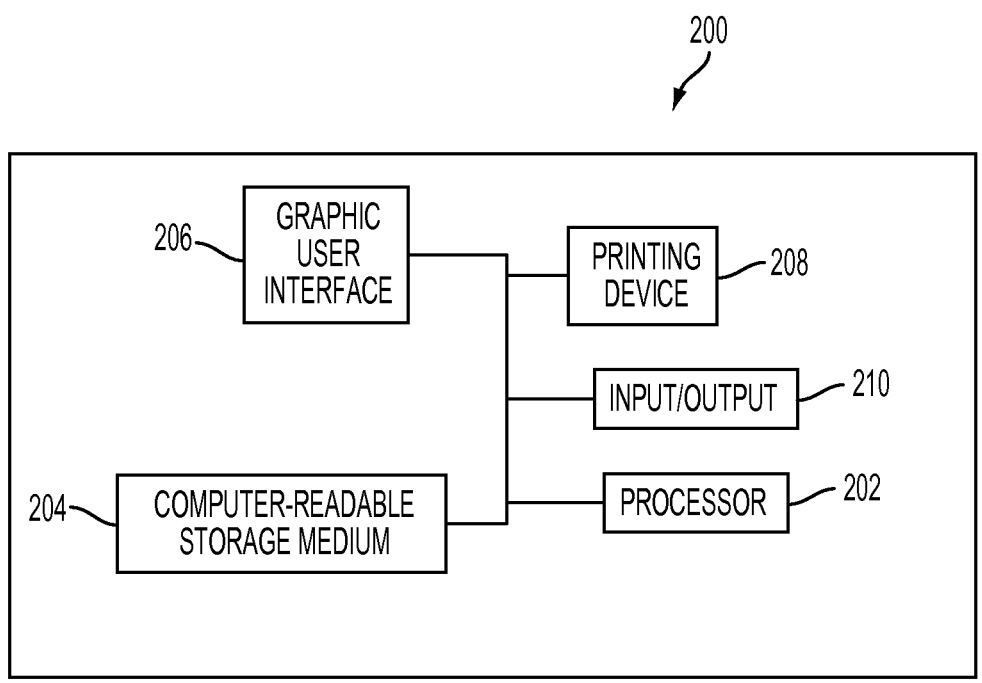
FIG. 2 is a schematic diagram of a system/apparatus according to embodiments herein.

System and device embodiments are shown in FIG. 2. Such systems 200 (which can be a special purpose computerized device or can be a general purpose device) include a processor 202 and a computer-readable storage medium 204 operatively connected to (directly or indirectly connected to) the processor 202. The computer readable-storage medium 204 stores instructions executable by the processor 202. A graphic user interface 206 is operatively connected to the processor. The graphic user interface 206 receives the instruction from the user to print the accumulation e-mail message. In addition, a printing device 208 and input/output connection 210 is operatively are connected to the processor 202. The input/output 210 can connect to other devices and/or networks to send and receive e-mail messages and print jobs.

The processor 202 executes the instructions to automatically identify boundaries between the e-mail messages within the accumulation e-mail message by matching pre-established header templates to text within the accumulation e-mail message, so as to identify the beginning point of each e-mail message and the ending point of each subsequent e-mail message.

For example, FIGS. 3A-3B illustrate 18 different types of exemplary header templates (301-318) that can recognize the beginning of an e-mail message. The headers are detected by parsing the e-mail file using the header models, or by keyword matching. One ordinarily skilled in the art would understand that these header templates 301-318 are merely examples and that the embodiments herein are not limited to the specific templates illustrated in FIGS. 3A-3B. Instead, any common e-mail header templates (whether currently known or developed in the future) could be included within the header templates that the embodiments herein can recognize so as to distinguish the ending point of one e-mail and the beginning point of an immediately adjacent e-mail.

The processor 202 also executes the instructions to automatically truncate the original e-mail message and one or more of the reply e-mail messages from the accumulation e-mail message to create the modified accumulation e-mail message. In doing so, the processor 202 is following the pre-established truncation rules set up by the user, which can be maintained within the computer-readable storage medium 204. The processor 202 further executes the instructions to automatically print the modified accumulation e-mail message using the printing device 208.

Therefore, the embodiments herein prevent unwanted (RE) reply-message printing. The system contains a user interface (UI), which receives users' preferences for e-mail printing, an e-mail segmenter, which locates boundaries between composing messages in an e-mail file, and a message cropper, which deletes the un-wanted portions before the e-mail is sent for printing. The user interface can be a standalone one, or a part of a printer driver user interface. It receives users' preference about e-mail printing. In particular, a user may specify the maximum number of pages per e-mail, maximum reply messages per e-mail, or a combination of both (e.g., 4 reply messages, but not exceeding 2 pages).

The user may set the specification on a per job basis, or set preferences as a default. Furthermore, the user may also request that warning messages be provided if an e-mail file is going to be cropped before printing to give the user the option to not have the automated truncation process continue.

If user's preference is specified purely in page number, un-wanted pages can be relatively easily deleted by locating the page boundaries. On the other hand, if the preference is given in number of messages, or a combination of page number and message number, the embodiments herein locate the boundaries between different messages.

Thus, with embodiments herein once the preferences are established (by the user or by manufacturer default). The only act required by the user is to issue a single print command. After the print command, the embodiments herein provide a completely automated process that selectively truncates e-mail messages according to the pre-established preferences.

Many computerized devices are discussed above. Computerized devices that include chip-based central processing units (CPU's), input/output devices (including graphic user interfaces (GUI), memories, comparators, processors, etc. are well-known and readily available devices produced by manufacturers such as Dell Computers, Round Rock Tex., USA and Apple Computer Co., Cupertino Calif., USA. Such computerized devices commonly include input/output devices, power supplies, processors, electronic storage memories, wiring, etc., the details of which are omitted herefrom to allow the reader to focus on the salient aspects of the embodiments described herein. Similarly, scanners and other similar peripheral equipment are available from Xerox Corporation, Norwalk, Conn., USA and the details of such devices are not discussed herein for purposes of brevity and reader focus.

The terms printer or printing device as used herein encompasses any apparatus, such as a digital copier, bookmaking machine, facsimile machine, multi-function machine, etc., which performs a print outputting function for any purpose. The details of printers, printing engines, etc., are well-known by those ordinarily skilled in the art and are discussed in, for example, U.S. Pat. No. 6,032,004, the complete disclosure of which is fully incorporated herein by reference. The embodiments herein can encompass embodiments that print in color, monochrome, or handle color or monochrome image data. All foregoing embodiments are specifically applicable to electrostatographic and/or xerographic machines and/or processes.

It will be appreciated that the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims. The claims can encompass embodiments in hardware, software, and/or a combination thereof. Unless specifically defined in a specific claim itself, steps or components of the embodiments herein cannot be implied or imported from any above example as limitations to any particular order, number, position, size, shape, angle, color, or material.

What is claimed is:

1. A method comprising:
   receiving an instruction to print an accumulation e-mail message through a graphic user interface of a computerized device, said accumulation e-mail comprising an original e-mail message and one or more reply e-mail messages made to said original e-mail message;
   in response to only said instruction to print, automatically identifying boundaries between said e-mail messages within said accumulation e-mail using said computerized device;
   in response to only said instruction to print, automatically truncating said original e-mail message and one or more of said reply e-mail messages from said accumulation e-mail message to create a modified accumulation e-mail message based on pre-established truncation rules and said boundaries using said computerized device; and
   in response to only said instruction to print, automatically printing said modified accumulation e-mail message using a printing device.

2. The method according to claim 1, further comprising receiving user truncation preferences to create said pre-established rules.

3. The method according to claim 1, one of said reply e-mail messages comprising a most recent e-mail message, and said truncating comprising removing all e-mail messages except said most recent e-mail message from said accumulation e-mail message to create said modified accumulation e-mail message.

4. The method according to claim 1, said original e-mail message and said reply e-mail messages comprising a historical chronology of replies made to said original e-mail message and to said reply e-mail messages.

5. A method comprising:
   receiving an instruction to print an accumulation e-mail message through a graphic user interface of a computerized device, said accumulation e-mail comprising an original e-mail message and one or more reply e-mail messages made to said original e-mail message;
   in response to only said instruction to print, automatically identifying boundaries between said e-mail messages within said accumulation e-mail message using said computerized device, said identifying of said boundaries comprising matching pre-established header templates to text within said accumulation e-mail message to identify a beginning point of each e-mail message;
   in response to only said instruction to print, automatically truncating said original e-mail message and one or more of said reply e-mail messages from said accumulation e-mail message to create a modified accumulation e-mail message based on pre-established truncation rules and said boundaries using said computerized device; and
   in response to only said instruction to print, automatically printing said modified accumulation e-mail message using a printing device.

6. The method according to claim 5, further comprising receiving user truncation preferences to create said pre-established rules.

7. The method according to claim 5, one of said reply e-mail messages comprising a most recent e-mail message, and said truncating comprising removing all e-mail messages except said most recent e-mail message from said accumulation e-mail message to create said modified accumulation e-mail message.

8. The method according to claim 5, said original e-mail message and said reply e-mail messages comprising a historical chronology of replies made to said original e-mail message and to said reply e-mail messages.

9. A computerized device comprising:
   a processor;
   a computer-readable storage medium operatively connected to said processor, said computer-readable storage medium storing instructions executable by said processor;
   a graphic user interface operatively connected to said processor receiving an instruction to print an accumulation e-mail message from a user, said accumulation e-mail comprising an original e-mail message and one or more reply e-mail messages made to said original e-mail message; and a printing device operatively connected to said processor, said processor executing said instructions to, in response to only said instruction to print, automatically identify boundaries between said e-mail messages within said accumulation e-mail message, said processor executing said instructions to, in response to only said instruction to print, automatically truncate said original e-mail message and one or more of said reply e-mail messages from said accumulation e-mail message to create a modified accumulation e-mail message based on pre-established truncation rules and said boundaries, and said processor executing said instructions to, in response to only said instruction to print, automatically print said modified accumulation e-mail message using said printing device.

10. The computerized device according to claim 9, said graphic user interface receiving user truncation preferences to create said pre-established rules.

11. The computerized device according to claim 9, one of said reply email messages comprising a most recent e-mail message, and said processor executing said instructions to automatically truncate said accumulation e-mail message by removing all e-mail messages except said most recent e-mail message from said accumulation e-mail message to create said modified accumulation e-mail message.

12. The computerized device according to claim 9, said original e-mail message and said reply e-mail messages comprising a historical chronology of replies made to said original e-mail message and to said reply e-mail messages.

13. A computerized device comprising:

a processor;

a computer-readable storage medium operatively connected to said processor, said computer-readable storage medium storing instructions executable by said processor;

a graphic user interface operatively connected to said processor receiving an instruction to print an accumulation e-mail message from a user, said accumulation e-mail comprising an original e-mail message and one or more reply e-mail messages made to said original e-mail message; and a printing device operatively connected to said processor, said processor executing said instructions to, in response to only said instruction to print, automatically identify boundaries between said e-mail messages within said accumulation e-mail message by matching pre-established header templates to text within said accumulation e-mail message to identify a beginning point of each e-mail message, said processor executing said instructions to, in response to only said instruction to print, automatically truncate said original e-mail message and one or more of said reply e-mail messages from said accumulation e-mail message to create a modified accumulation e-mail message based on pre-established truncation rules and said boundaries, and said processor executing said instructions to, in response to only said instruction to print, automatically print said modified accumulation e-mail message using said printing device.

14. The computerized device according to claim 13, said graphic user interface receiving user truncation preferences to create said pre-established rules.

15. The computerized device according to claim 13, one of said reply email messages comprising a most recent e-mail message, and said processor executing said instructions to automatically truncate said accumulation e-mail message by removing all e-mail messages except said most recent e-mail message from said accumulation e-mail message to create said modified accumulation e-mail message.

16. The computerized device according to claim 13, said original e-mail message and said reply e-mail messages comprising a historical chronology of replies made to said original e-mail message and to said reply e-mail messages.

\* \* \* \* \*